United States Patent [19]
Tunney

[11] 3,989,039
[45] Nov. 2, 1976

[54] FACIAL MUSCLE COMPRESSOR
[76] Inventor: Lora Tunney, P.O. Box 633, Patchogue, Long Island City, N.Y. 11772
[22] Filed: Aug. 7, 1975
[21] Appl. No.: 602,835

Related U.S. Application Data
[63] Continuation of Ser. No. 499,757, Aug. 22, 1974, abandoned.

[52] U.S. Cl. .................................. 128/76 C
[51] Int. Cl.² .................................. A61F 5/08
[58] Field of Search ............. 128/76 C, 76 R, 346, 128/132

[56] References Cited
FOREIGN PATENTS OR APPLICATIONS
20,358   12/1895   United Kingdom ............... 128/76 C
274,006   7/1927   United Kingdom ............... 128/76 C
6,743    7/1904   United Kingdom ............... 128/76 C Primary Examiner—John D. Yasko

[57] ABSTRACT
A facial muscle compressor is disclosed for controlling the widening of nose and nostrils. Clip-like means having a pair of padded jaw members is disclosed for attachment to a nose.

1 Claim, 3 Drawing Figures 3,989,039

FACIAL MUSCLE COMPRESSOR

This is a continuation of application Ser. No. 499,757 filed Aug. 22, 1974, now abandoned.

SUMMARY OF THE INVENTION

The device disclosed when properly used exerts a gentle constricting pressure on the nose and for that purpose is placed on the nose causing a firming, shaping-up and restoring of the tone of the nose muscle. The invention comprises generally a novel new use whereby means of a padded clamp or clip-like device with c spring is used. Clip-like means are provided for securing the device to the wearer's nose and easily held in place. The finger pieces, when engaged, open the jaws, the device is then centrally placed over the nose and nostrils area and when the finger pieces are disengaged the controlling firming action on the nose and nostrils begins, the jaws becoming gently clamp-like on the nose. In order that the device may be comfortable and have non-slip adherence qualities and avoid any possible abrasion during its wear, it is almost entirely thinly padded of a soft plushy padding which is attached by stitching or glueing to the device. For further comfort, two flaps approximately one inch at the bottom part of the jaw-like free ends are provided which create a desired protective cushioning effect preventing any possible digging in the surrounding skin area, said flaps are extensions of the padding material.

BRIEF DESCRIPTION OF THE DRAWING

In the drawing, like reference characters designate similar parts in the several views.

DESCRIPTION OF THE PREFERRED EMBODIMENT

This invention relates to a facial muscle compressor whose primary object is concerned with gently constricting and controlling the nose and nostrils—as a cosmetic aid to men and women—to delay and minimize the spread and widening of the nose and nostrils.

Another object is for improving facial appearance.

A still further object is to provide such means that are positive in operation, convenient and comfortable in use, easily placed on the nose and easily disengaged therefrom, economical of manufacture, relatively simple and of general serviceability. This invention also comprises novelty of use and combination which will more fully appear in the course of the following description, which is based on the accompanying drawing. However, said drawing merely shows and the following description merely describes one embodiment of the present invention, which is given by way of illustration or example only.

Figure 1:
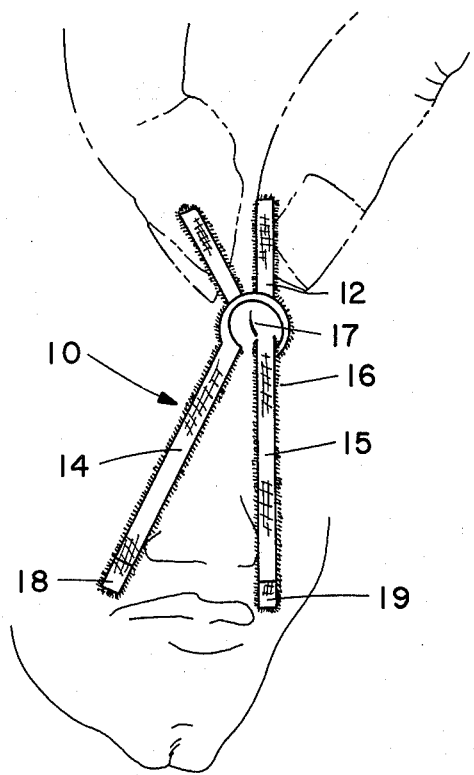
FIG. 1 is an enlarged perspective front view showing the manner of applying the present facial muscle compressor.
Figure 3:
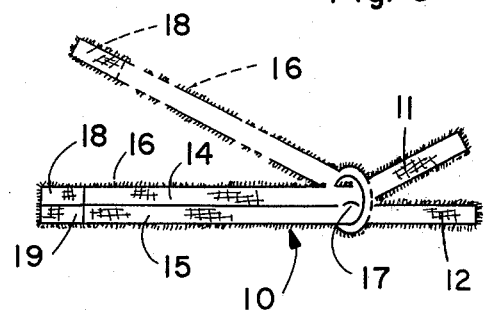
FIG. 3 is a sectional view of the nose engaging means of the present device, embodying the invention, the jaws being shown in the closed position in full lines, and in the open position in dotted lines.

With reference to the drawing, as illustrated in FIG. 1 the almost entirely padded facial muscle compressor 10 comprises a clip-like means consisting of an upper finger piece member 11 and a lower finger piece member 12 said finger piece members being extension of the jaws 14 and 15 said jaws being of the same length and width, with jaw member 14 supported on the lower jaw member 15. The jaw members 14 and 15 and finger piece members 11 and 12 are narrow elongated members with finger piece member 11 having an end section angularly offset in a vertical direction from the plane in which the other end or jaw 14 lies. The finger pieces 12 has an end section at one end which is in the same plane as a jaw section 15 at the other end thereof. The finger piece members 11 and 12 are secured together by a C spring 17 at the proximal end of the finger piece extension members 11 and 12 with the jaw 14 lying on the jaw 15 as illustrated in FIG. 3 so that when the end sections of the finger pieces 11 and 12 are compressed toward one another the jaw members 14 and 15 open and when placed on the nose said jaws 14 and 15 become a clamp on the nose. The device 10 is almost entirely padded with a soft preferably plushy padding 16 except for the portions where the C springs 17 and the inner portion area of the finger pieces 11 and 12. Also illustrated is an upper flap 18 and a lower 19, said flaps are an extension preferably one inch of the same material as the rest of the padding but is substantially the same width as at the free ends at the bottom of the jaws 14 and 15. The soft padding is preferably of a soft plushy material 16 sewed or glued along where illustrated in the drawings, said padding or the like providing the clip-like device to be maintained in position while on the wearer's nose, under snug yet comfortable tension since it acts as a non-slippery agent, and prevents the device 10 from being liable to slip out of position.

Figure 2:
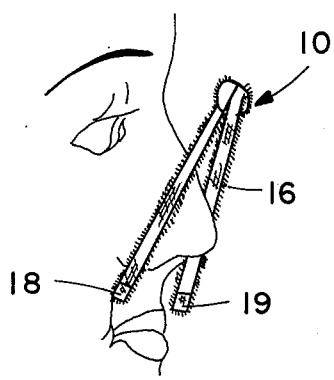
FIG. 2 is a perspective side view showing the device when placed on a wearer's nose.

FIGS. 1 and 2 illustrate the use of the padded facial muscle compressor 10 which is manually placed on the nose, as described, for exerting pressure on the nose and nostrils when the finger pieces 11 and 12 open the jaws 14 and 15 and the nose is clamped between the jaws 14 and 15.

FIG. 3 shows a view of the padded device embodying the invention, which is designated by the numeral 10 the jaws 14 and 15 being shown in the closed position in full lines and in the open position in dotted lines. Also illustrated are padding 16 and flaps 18 and 19 said flaps being an extension preferable one inch of the same material as the padding 16 situated below the jaws 14 and 15.

The user of the facial muscle compressor 10 merely places same centrally over the nose and nostrils squeezing the finger pieces 11 and 12 then relaxing the finger pieces 11 and 12 thus starting a gentle pressure with the nose between the jaws 14 and 15 of the device. This pressure as applied against the nose and nostrils is found to have beneficially effect on the nose and nostrils.

While the foregoing has illustrated and described what is now contemplated to be the best mode of carrying out the invention, the embodiments of the invention, are, of course, subject to modification without departure from the spirit and scope of the invention. Therefore, it is not desired to restrict the invention to the particular form of construction illustrated and described, but to cover all modifications that may fall within the scope of the appended claim. All is new and novel whereby means of a novel padded clip-like structure with C spring in combination is used.

What is claimed is:

1. A facial muscle compressor for controlling the widening of nose and nostrils and means to maintain said compressor on the nose, in a combination of a clip like means together with a padding means, the latter for maintaining said compressor on the nose comfortably, for sufficient periods of time, in combination comprising:

a clip like means consisting of a pair of narrow elongated jaw members, with finger piece extensions, one of said jaw members juxtaposed above the other jaw member with a C spring joining said jaw members together near the finger piece ends thereof, one finger piece having one end thereof angularly spaced in a vertical direction from said one end to said C spring, whereby compression of said angular offset section of said one finger piece toward said other finger piece will cause the other end of one jaw to be spaced from said other jaw thereby to accept a nose thereinbetween, said jaw members and extension finger pieces being covered with a cushioning soft plushy padding material attached onto almost the entire device, said padding means provided for the purpose of maintaining the compressor on the nose, for comfort and to eliminate danger of abrasion to the skin, further, a flap means is attached to each jaw member which extends at the bottom part of the free ends of the jaw members, made of a soft plush padding material.

* * * * *